United States Patent
Meilahn et al.

(10) Patent No.: US 6,326,043 B1
(45) Date of Patent: Dec. 4, 2001

(54) METHOD FOR MEASURING PROCESSING DEGREE AND GELATINIZED STARCH CONTENT OF STEAM-FLAKED CORN AND OTHER GRAINS

(76) Inventors: Marcus K. Meilahn, 2723 Buena Vista Dr., Greeley, CO (US) 80631; Davy R. Brown, 26778 WCR 36, LaSalle, CO (US) 80645

( * ) Notice: Subject to any disclaimer, the term of this patent is extended or adjusted under 35 U.S.C. 154(b) by 0 days.

(21) Appl. No.: 09/447,699

(22) Filed: Nov. 23, 1999

Related U.S. Application Data

(60) Provisional application No. 60/112,627, filed on Dec. 16, 1998.

(51) Int. Cl.$^7$ .............................. A23P 1/14; G01N 33/10
(52) U.S. Cl. ........................... 426/461; 426/625; 435/14
(58) Field of Search .............................. 426/560, 18, 28, 426/450, 457, 511, 231, 549, 625, 460, 461, 462; 435/14, 22

(56) References Cited

PUBLICATIONS

Xiong et al., *J. Animal Sci.*, 68: 3861–3870, 1990.*
Xiong et al., *J. Animal Sci.*, 68: 3880–3885, 1990.*
Xiong et al., *J. Animal Sci.*, 69: 1707–1718, 1991.*

* cited by examiner

*Primary Examiner*—Keith Hendricks
(74) *Attorney, Agent, or Firm*—Dean P. Edmundson

(57) ABSTRACT

The nutritive value of flaked grain can be quantified by measuring starch availability, degree of processing, and the percentage of gelatinized starch in relation to the total amount and availability of starch in the whole (unprocessed) grain. A laboratory method is described for measuring the degree of processing and starch gelatinization. The method utilizes the differences in reaction rates between corn starch and gelatinized corn starch, for example. The method involves determining the relationship between glucose yield and gelatinized starch percent of known reference standards and flaked grain samples. The data are then used to provide valuable information used to adjust milling practices.

2 Claims, 3 Drawing Sheets

Figure 1:
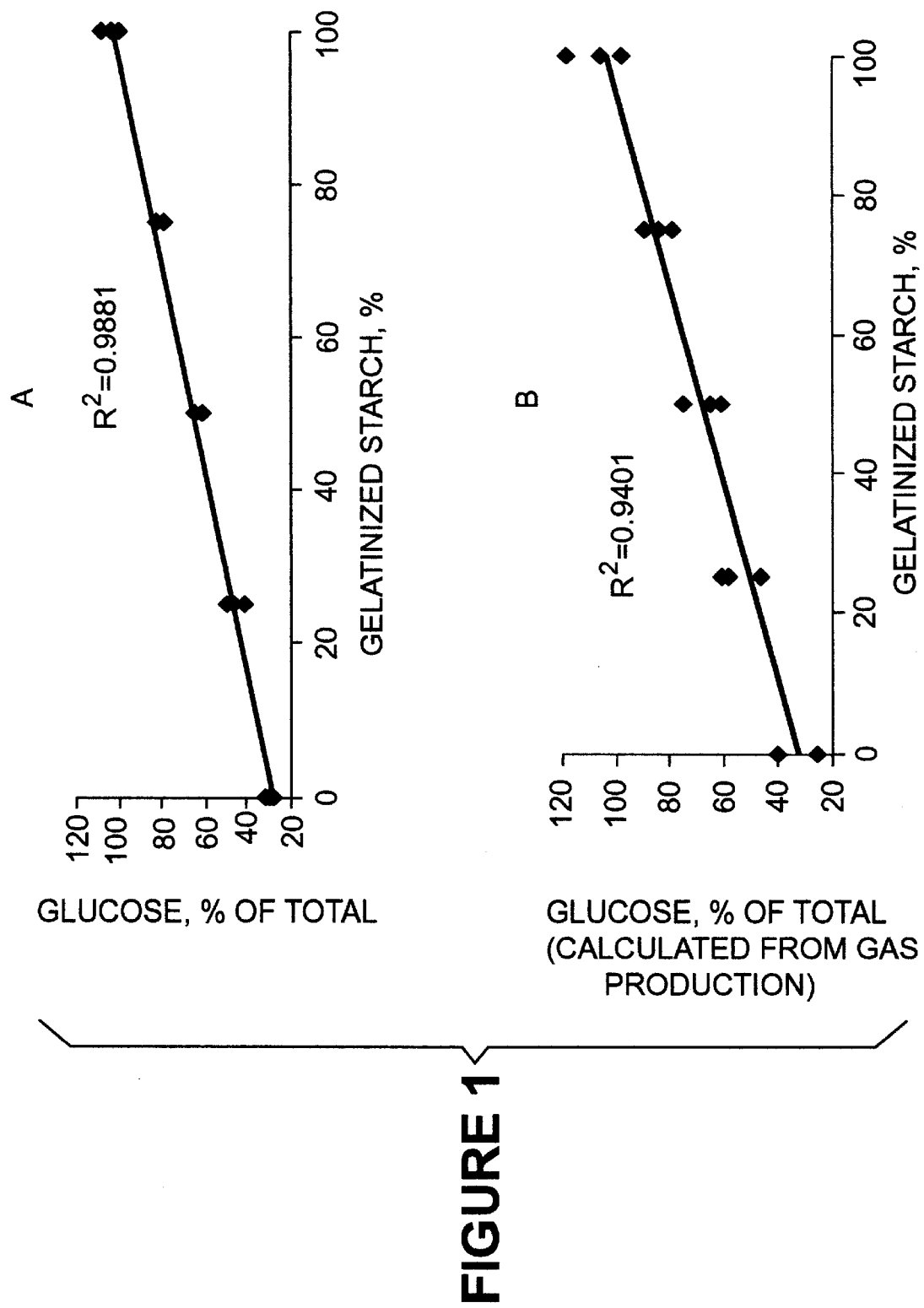

METHOD FOR MEASURING PROCESSING DEGREE AND GELATINIZED STARCH CONTENT OF STEAM-FLAKED CORN AND OTHER GRAINS

CROSS-REFERENCE TO RELATED APPLICATION

This application is based upon and claims the benefit of our Provisional Application No. 60/112,627, filed Dec. 16, 1998.

FIELD OF THE INVENTION

This invention relates to processing of corn and other grains. More particularly, this invention relates to techniques for measuring the degree of processing and the gelatinized starch percentage of feed grains.

BACKGROUND OF THE PRIOR ART

Properly steam flaking corn can improve its nutritive value from 3 to 10% depending on the percent damaged grain, moisture content, fines, flake density, etc. (Karr, 1984, Zinn, 1990ab). An average improvement of 6% from correctly steam flaking corn potentially realized an estimated $750 thousand (to as much as $1.5 million) annually on 30 thousand head of feedlot cattle (Karr, 1984). Karr (1984) also reported the cost of a feedlot producing flakes with a density of 22 lbs/bu would be approximately $6.67/ton compared with $3.33/ton for flakes weighing 29 lbs/bu. Smith and Richardson (1996) reported the electrical cost of flaking corn at steam times of 20, 30, and 40 min was $2.30, $1.40, and $2.30 per ton for flakes weighing 26.0, 26.1, and 27.0 lbs/bu, respectively. They reported that after 40 min of steaming, the time required to roll 50 lbs of corn increased because of increased doughing on the rolls possibly because of overcooking the starch. This may also partially explain the increase in the cost of flaking corn steamed for 40 minutes.

Zinn (1 990a) examined the influence of steaming time on the digestion of flaked corn in steers consuming 75% corn diets (intake was restricted indicating digestibility may be higher than that observed for cattle consuming free choice). He compared steaming times of 34, 47, and 67 minutes and flaked corn to a density of 25–26 lbs/bu. Moisture uptake was similar for corn steamed at 34 and 47 minutes, averaging 5%. Moisture uptake by corn steamed for 67 minutes was 8% (i.e. significantly higher). Zinn (1990a) indicated the initial 3 to 5 percentage unit increase in moisture occurs very quickly following application of steam and that moisture greater than 5 percentage units requires prolonged exposure to steam. Prolonged steaming and/or lack of penetration increases external moisture on the corn kernel which too contributes to doughing on the rolls (Karr, 1984). In general, steaming corn longer than 34 minutes did not increase the nutritive value of the corn and total G.I. tract digestibility of starch was essentially complete (99.5%) for steam flaked corn steamed for 34 minutes.

The main purpose for steam flaking is to increase the digestibility of the starch and to maximize net energy intake by the cattle. Feedlot growth trials have shown steam flaking will increase the energy value of corn over that of dry rolling from 13 to 16 % (Zinn, 1987). The degree improvement in starch but not performance has been linearly related to flake thickness and/or density (Osman et al., 1970, Zinn, 1990b). Zinn (1990b) compared the feeding value of corn steam flaked to densities of 28, 24, and 20 lbs/bu. He reported flake density was directly related to thickness and inversely related to in vitro enzymatic starch digestibility (IVSD) and suggested the relationship between IVSD and in vivo starch digestion may be casual rather than causal. Ruminal and total tract starch digestibility increased with decreasing flake density but was of a small magnitude (1.1%) for flakes weighing 28 compared with 20 lbs/bu. Therefore, differences in digestibility between flakes weighing 24 and 20 lbs/bu would likely be even less.

Feedlot performance did not differ for steers fed diets containing corn flaked to densities of 28, 24, and 20 lbs/bu (Zinn, 1990b). In fact, Zinn (1990b) reported a tendency for slower weight gain, and reduced feed efficiency by steers fed steam flaked corn of the lowest density (20 lbs/bu). Steers consuming the lighter flakes had significantly lower ruminal pH, suggesting digestive dysfunction and reduced performance of some individual animals in the study. Variation in weight gain for steers consuming the 20 lbs/bu flake was 366% greater than the average for both groups of steers consuming the 24 and 28 lbs/bu flakes which suggests the variability in weight gain was due to the variable effects of 20 bushel weight corn on gastrointestinal tract function and subsequent performance. In addition to digestive dysfunction, the tendency toward reduced performance by cattle consuming flakes of the lowest density was attributed to reduced intake and consequent reduced weight gain rather than lower feed conversion. This type of situation was addressed by Karr (1984) who suggested if grain utilization is improved 15% we would hope feed consumption would not decrease more than 8% so that a faster rate of gain could be attained through greater net energy intake.

Many factors influence starch availability (i.e. degree of processing) including corn quality, tempering conditions, cook time, cook temperature, roll condition, and flake density. Unfortunately, commercially available methods that are currently being used to measure processing degree of grain are unreliable and unscientific. Flaking corn is an expensive process; too little processing may produce flakes with only little improvement in starch availability, while over-processing may produce flakes with very high starch availability, thereby increasing production costs and the potential for digestive upset with little if any improvement in cattle performance.

The most common commercially available method for determining starch availability is to simply measure gas production by yeast fermentation. Many commercial laboratories provide this service; however, methods and results vary greatly between and within laboratories due in part to differences in methodology, enzyme activity, and lack of use of a meaningful standard and an accounting of initial corn quality. For example, laboratory results will vary because the total starch content of corn varies between areas and seasons, and because the activity of enzymes will vary between suppliers as well as pH. If an attempt to control these sources of variation is not made, then estimates of starch availability (or degree of processing, or percent gelatinization) are highly variable due to the corn itself and laboratory methodology rather than milling practices. Therefore, it is not surprising why results will vary widely between and within laboratories, which may serve only to confuse and frustrate the miller.

DISCLOSURE OF THE INVENTION

In order to minimize variation in results, the present invention provides a method for chemically analyzing the processing degree of corn (or other grains). The method has been developed to provide a reliable commercially available procedure for the routine evaluation of processed grains. "Degree of processing" is defined herein as the amount of glucose available to enzymatic hydrolysis in the processed grain relative to the total amount of glucose measured in the whole grain (or in processed grain if the total amount of glucose in the processed grain is used, but results may slightly differ compared with those determined from whole grains).

As with biological fluids, this procedure is principally based on the following coupled enzymatic reactions:

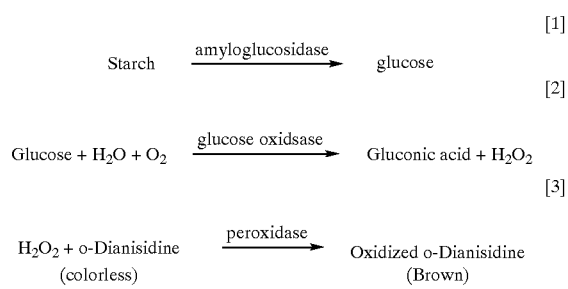

The intensity of the brown color measured at 450 nm is proportional to the original glucose concentration in the sample (Sigma diagnostics, Glucose procedure No. 510).

To determine the degree of processing (DOP) in grain samples, the samples must first be dried at 60° C. for 24 to 48 hours and subsequently ground to pass a 1 mm screen. After grinding, whole corn samples are pressure cooked for 1 hour at 15 p.s.i. for the determination of total starch content. Flaked (i.e. processed) grains are not pressure cooked, so that glucose availability due to milling or processing conditions can be determined. Once prepared for wet chemistry, all samples are incubated (39° C.) in buffered solution (pH 4.5) containing amyloglucosidase for precisely 6 hours. After 6 hours of incubation, the quantity of starch susceptible to enzymatic hydrolysis is determined colorimetrically for both the whole and processed corn (grain) sample. The degree of processing is then calculated using the following equation:

Degree of processing=available glucose/total glucose×100(processed grain)/(whole grain)      [Eq. 1]

Once the DOP has been determined, the percentage of gelatinized starch may be estimated; this is a totally unique feature of our method. Using our reference samples made from mixtures of intact and gelatinized starch, the relationship between glucose yield and gelatinization percent can be determined (See FIG. 1). This regression equation (Y=mx+b) can then be rearranged ((Y−b)/m)=x)) and used to estimate the percentage of gelatinized starch in the actual processed grain sample using equation 2 below:

Gelatinization percentage=(DOP, %−intercept)/slope      [Eq. 2]

The method that we have developed depends upon the differences in reaction rates between corn starch and gelatinized corn starch, for example. It will also detect other subtle physical and chemical changes that makes the processed corn starch more readily available to enzymatic activity. Other methods may be useful in this invention using reaction rates and other enzymes, but such variations are considered to be within the scope of this invention. The method should be subject to enzyme activity; however, we are comparing the enzyme activity to both standards. As such, the enzyme activity is not being measured; rather, the reactivity of the standards is being measured against a "constant" enzyme. If a more reactive enzyme is used, it should enhance the rate of the starch and the gelatinized starch by the same factor. Although a different relationship will be observed, one should still obtain the correct results. Temperature, pH (buffers), time, and concentration will also affect the rates; however, these will affect both standards similarly.

Preparation of Standards

Commercial corn starch is dried in a forced-air oven for 48 hours at 60 to 65 C.

Gelatinized corn starch is prepared by subjecting commercial corn starch to a hot water treatment (70 to 75 C.) using a ten to one ratio of water to corn starch for a specified time. The gelatinized corn starch solution is then frozen and the water removed by freeze drying to yield the solid, gelatinized corn starch. This material is less than one percent birefringent and the granules match published pictures of gelatinized corn starch. This material is oven dried for 48 hours at 60 to 65 C. in a forced-air oven. The oven dried standards are stored in a desiccator.

Preparation of Standard Mixtures and Reactivity Relationship

The standard mixtures are prepared by weighing out standards to the nearest milligram and placing them in the reaction vessel. For example, the 50% starch and 50% gelatinized mixture is prepared by weighing 50.0 milligrams of corn starch and 50.0 milligrams of gelatinized corn starch. Several standard mixtures were prepared (i.e. 100% intact starch/0 % gelatinized starch; 75% intact/25% gelatinized; 50%/50%; 25%/75% and 0%100%). The reactivity relationship between corn starch and gelatinized corn starch is obtained by plotting the amount of glucose liberated from each standard on one axis and the percent of gelatinized starch on the other axis. The amount of glucose liberated is described below.

Liberation of Glucose from Corn Starch, Gelatinized Corn Starch, Standard Mixtures, and Flaked Corn Samples The ground corn samples and the starch standards, typically 100.0 milligrams, are placed into a 50 mg Erlenmeyer flask and 9.0 ml of an acetate buffer (pH 4.5) and 1.0 ml of an enzyme which liberates glucose from starch are added. The flask is sealed with parafilm and incubated at 40 C. for six hours. At the end of the reaction, the amount of glucose in each sample is determined using a modified Sigma Diagnostics Glucose procedure or any accurate, equivalent method.

Performance characteristics

The relationship between glucose yield (i.e. available starch) and gelatinization percentage was determined using our method (DOP) versus the gas production method; data are summarized in FIGS. 1a and 1b. Variation in glucose yield was reduced 56% (4.02 versus 9.03) when measured using DOP (FIG. 1a) compared with gas production (FIG. 1b).

Figure 2:
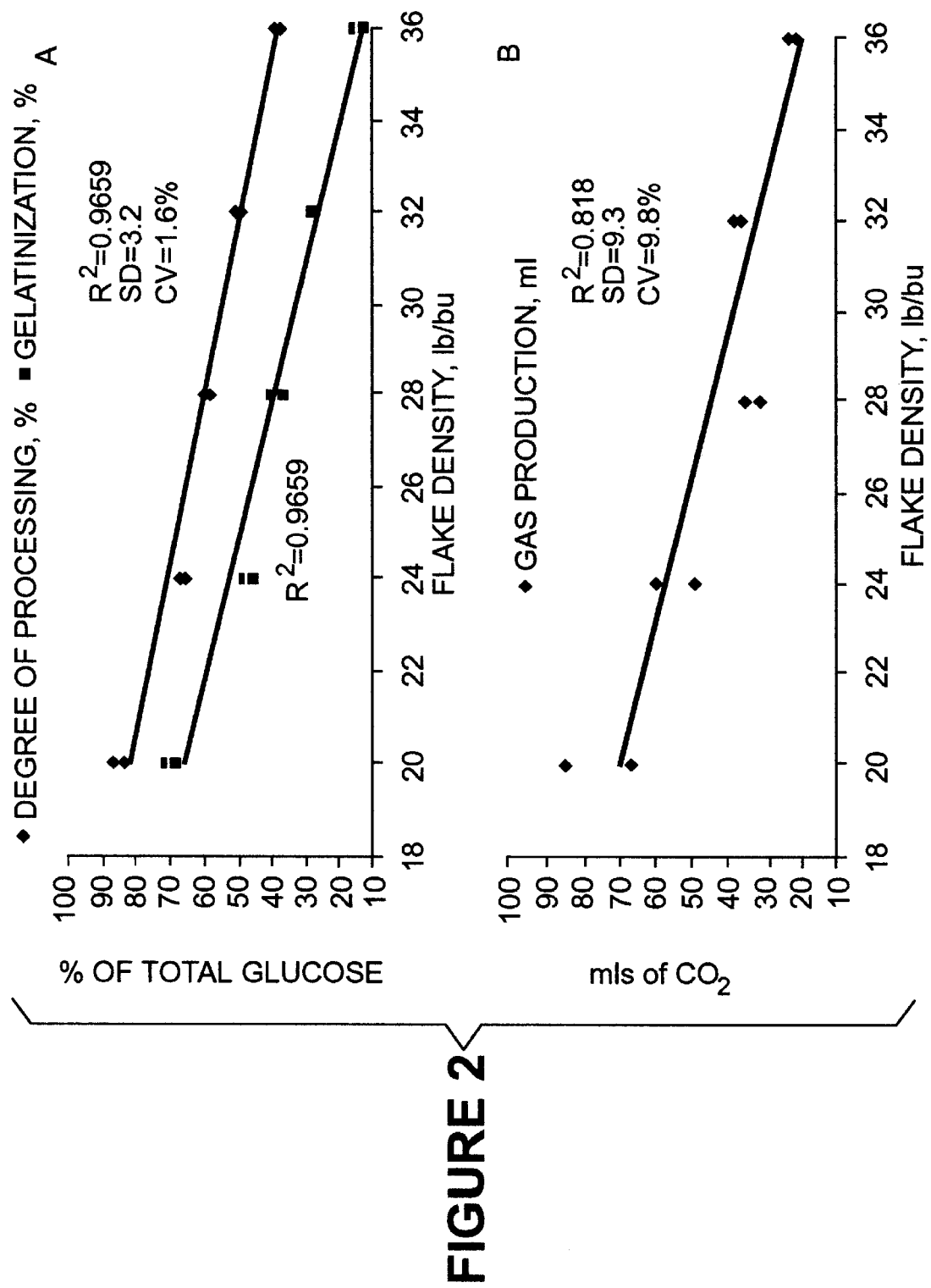

Similarly, starch availability of corn steam-flaked to five different flake densities was 56% less variable when measured in duplicate using DOP compared with that determined using gas production (FIGS. 2a and 2b).

Starch availability decreased linearly (P<0.001) with increasing flake density, regardless of method. However, the coefficient of variation (CV%) between duplicates averaged 1.6% and 9.8% (84% reduction) for DOP compared to conventional gas production, respectively. Gelatinization percentage (FIG. 2a) also decreased with increasing flake density ($P<0.001$) with an average CV% of 1.58. Gelatinization percentage cannot be estimated using conventional gas production methodology (FIG. 2b); consequently, no estimates of gelatinization percentage were reported for that method.

Figure 3:
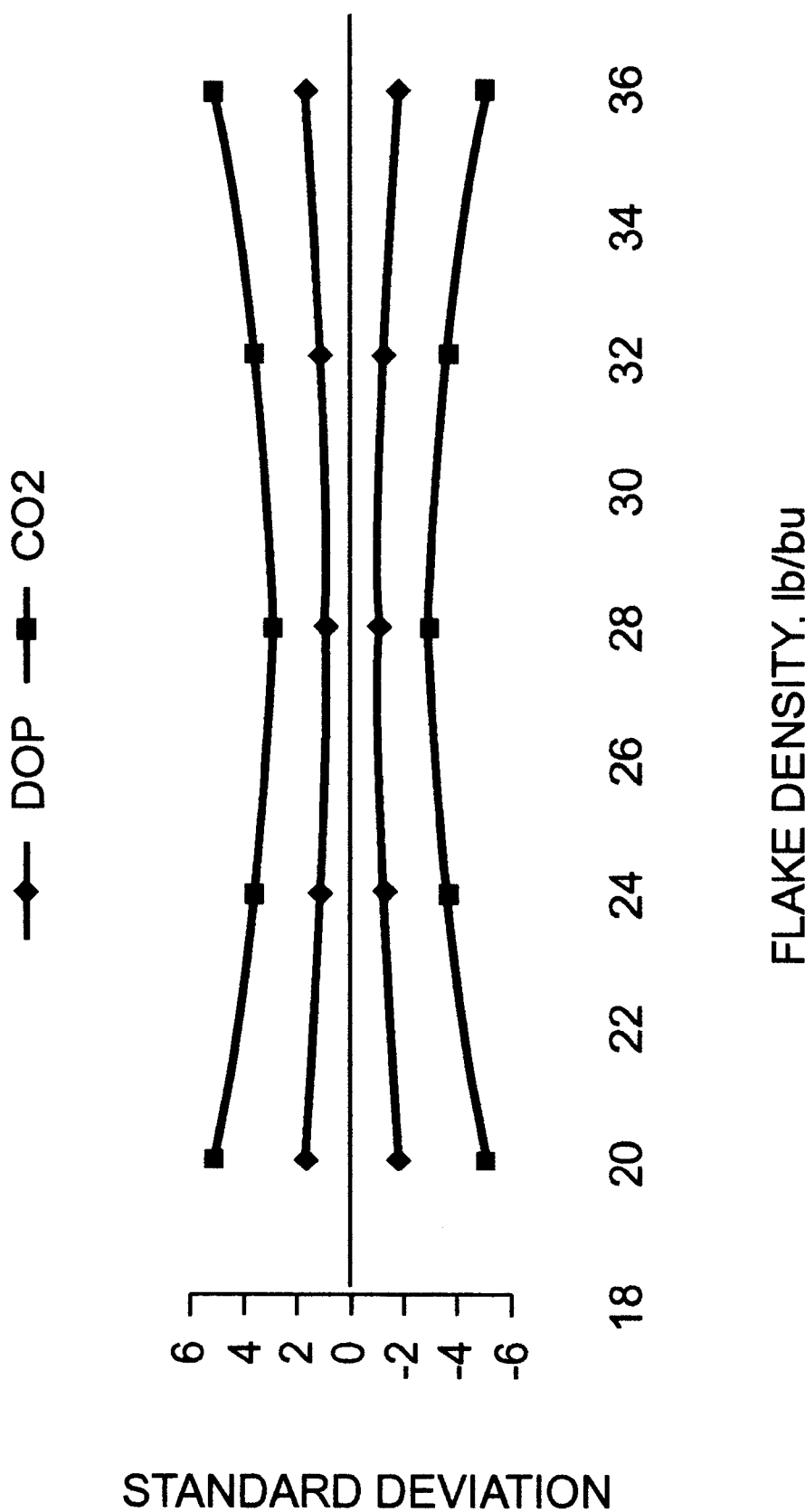

The range of standard deviations (SD) associated with DOP was much narrower (56% on average) compared with that determined using gas production (FIG. 3). The SD of our method was lowest (SD±1.01) for flakes weighing 28 1b/bu and became larger as flake density changed in either direction to a maximum of ±1.74 for flakes weighing 20 and 36 lb/bu (FIG. 3).

Other variants are possible without departing from the scope and spirit of this invention. Other enzymes may be used, and the techniques described herein are useful when analyzing all types of grains. The methods and techniques of this invention are useful in connection with any starch-containing material, e.g. grains (e.g. wheat, barley, sorghum, corn, etc.) and other starch-containing materials.

What is claimed is:

1. A process for preparing and using pure reference standards for estimating gelatinized starch content in a selected steam-flaked grain sample, comprising the steps of:

(a) preparing a plurality of reference standards containing known proportions of intact starch and gelatinized starch;

(b) enzymatically measuring the glucose yield as a percentage of total glucose in each said reference standard under set conditions;

(c) establishing the relationship between the percentage of glucose yield to total glucose, and the percentage of gelatinized starch obtained from each reference standard, by plotting said percentage values to correspond on a graph prepared with separate axis designated as (1) the glucose yield as a percentage of total glucose, and (2) the percentage of gelatinized starch;

(d) enzymatically measuring the yield of glucose as a percentage of total glucose in a steam-flaked grain sample under the same set conditions as used in step (b); and (e) plotting the value of the yield of glucose percentage for the steam-flaked grain sample from step (d) on the graph prepared in step (c), and comparing said steam-flaked grain value to the values of the reference standards found therein, to estimate the corresponding percentage of gelatinized starch in said steam-flaked grain sample.

2. A method for estimating the percentage of gelatinized starch in steam-flaked grain sample, comprising the steps of:

(a) providing a plurality of reference standards containing known proportions of intact starch and gelatinized starch;

(b) enzymatically measuring the yield of glucose as a percentage of total glucose in each said reference standard under set conditions;

(c) establishing the relationship between the percentage of glucose yield to total glucose, and the percentage of gelatinized starch obtained from each reference standard, by plotting said percentage values to correspond on a graph prepared with separate axis designated as (1) the glucose yield as a percentage of total glucose, and (2) the percentage of gelatinized starch;

(d) measuring the total glucose content of a non-flaked grain sample;

(e) measuring the amount glucose which is susceptible to enzymatic hydrolysis, under the same set conditions as used in step (b), of a steam-flaked grain sample which corresponds to the non-flaked grain sample of part (d) which has been steam-flaked.

(f) dividing the glucose amount determined in step (e) by the total glucose content from step (d) and multiplying by 100 to obtain the yield of glucose as a percentage of total glucose in the steam-flaked grain; and (g) plotting the value of the yield of glucose percentage for the steam-flaked grain sample from step (f) on the graph prepared in step (c), and comparing said steam-flaked grain value to the values of the reference standards found therein, to estimate the corresponding percentage of gelatinized starch in said steam-flaked grain sample.

* * * * *